United States Patent [19]

Phillips et al.

[11] 3,998,829

[45] Dec. 21, 1976

[54] STEROID ANAESTHETICS OF THE PREGNANE AND 19-NORPREGNANE SERIES

[75] Inventors: Gordon Hanley Phillips, Wembley; Robin Lawrence, London; Leslie Stephenson, London; Barry Edward Ayres, Amersham, all of England

[73] Assignee: Glaxo Laboratories Limited, Greenford, England

[22] Filed: May 8, 1973

[21] Appl. No.: 358,381

[30] Foreign Application Priority Data

May 12, 1972 United Kingdom ............ 22489/72

[52] U.S. Cl. .................. 260/239.5; 260/239.55 R; 260/397.4; 260/397.1; 260/397.45; 260/397.3

[51] Int. Cl.$^2$ ........................................ C07J 43/00

[58] Field of Search ................... 260/397.45, 239.5; /Machine Searched Steroids

[56] References Cited

UNITED STATES PATENTS

| 3,042,691 | 7/1962 | Hess et al. .................... 260/397.47 |
|---|---|---|
| 3,176,012 | 3/1965 | Bertin .......................... 260/239.55 |
| 3,463,776 | 8/1969 | Lester et al. ................. 260/239.57 |
| 3,661,940 | 5/1972 | Coombs et al. ............... 260/397.3 |
| 3,714,352 | 1/1973 | Davis et al. ........................ 424/243 |
| 3,862,194 | 5/1973 | Woods .......................... 260/397.45 |
| 3,883,569 | 5/1975 | Phillips et al. ................ 260/397.45 |

OTHER PUBLICATIONS

Fieser et al., Steroids pp. 692–696 (1959).
P'an et al., Methods in Hormone Research vol. 3 pp. 415–422 (1964).

Primary Examiner—Elbert L. Roberts
Attorney, Agent, or Firm—Bacon & Thomas

[57] ABSTRACT

Steroid anaesthetics of the pregnane and 19-norpregnane series are described, the compounds possessing a 3α-hydroxy group, a 5α-hydrogen atom or a 4,5-double bond, a 17α-hydrogen atom, a 20-oxo group and at the 21-position a hydrocarbon group which may be substituted by an oxo, ether, hydroxy, acyloxy, esterified carboxy, thioether, thioester, heterocyclic, amino or aromatic group, or a fluorine or chlorine atom. The acetals and 20-enol ethers of compounds having a 21-formyl group are also described.

11 Claims, No Drawings

STEROID ANAESTHETICS OF THE PREGNANE AND 19-NORPREGNANE SERIES

This invention is concerned with compounds of the pregnane series having anaesthetic activity.

It has long been known that number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard or disadvantage. The literature shows that very many steroid compounds have been studied in this regard. Reviews and discussions of some of the work carried out are to be found, for example, in "Methods in Hormone Research" (Edited by Ralph I. Dorfman, Vol. III Part A, Academic Press, London and New York, 1964, pages 415–475); H. Witzel, Z. Vitamin Hormon-Fermentforsch 1959, 10, 46–74; H. Selye, Endocrinology, 1942, 30, 437–453; S. K. Figdor et al., J. Pharmacol. Exptl. Therap., 1957, 119, 299–309 and Atkinson et al., J. Med. Chem. 1965, 8, 426–432.

A thorough review of the literature indicates that many anaesthetic steroids possess poor activity and/or long induction periods. A variety of undesired side effects such as paraesthesia and vein damage have also been noted.

We have found useful anaesthetic acitvity in a new group of pregnane steroids.

Thus the invention provides steroids of the pregnane or 19-norpregnane series possessing a $3\alpha$-hydroxy group, a $5\alpha$-hydrogen atom or a 4,5-double bond, a $17\alpha$-hydrogen atom, a 20-oxo group, and at the 21-position at least one monovalent or divalent straight, branched or cyclic hydrocarbon group (for example an alkyl, cycloalkyl or alkenyl group, an alkylidene group or a divalent alkylene chain, all preferably having 1–6 carbon atoms), which may be unsubstituted or carry at least one oxo, ether, hydroxy, acyloxy or esterified carboxy group, a C-attached nitrogen containing heterocyclic group, a thioether or thioester group, a chlorine or fluorine atom, an aromatic group or an N-attached residue of a primary or secondary amine or ammonia. The hydrocarbon group may be monovalent or a divalent group such as an alkylidene group (e.g. methylene) or a divalent alkylene group such as 1,2-ethylene group.

In general the steroid preferably carries at the 20-position a group of the formula $-CHR^1R^2$ where $R^1$ represents a hydrogen atom or an alkyl or esterified carboxyl group; and when $R^1$ is a hydrogen atom, $R^2$ is an alkyl group or an alkyl group substituted by an N-attached residue of a primary or secondary amine or ammonia, or a hydroxyl, alkoxy, acyloxy, thioether or thioester group, a chlorine or fluorine atom or is an esterified carboxyl group or an acyl group (including a formyl group) or a group of the formula

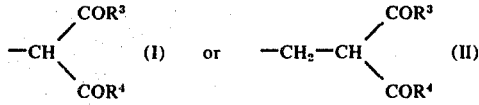

where $R^3$ and $R^4$ are the same or different and are alkyl or alkoxy groups; and, when $R^1$ is an alkyl group, $R^2$ is an alkyl group; and, when $R^1$ is an esterified carboxyl group, $R^2$ is an esterified carboxyl group; and where $R^1$ and $R^2$ may represent an alkylidene group or taken together with the 21-carbon atom may represent a cyclopropyl group. The invention also includes the acetals and 20-enol ethers of the compounds wherein $R^2$ is a formyl group; it also includes salts formed by the acidic or basic compounds of the invention.

It will be appreciated that acyl and esterified carboxyl groups may be regarded as hydrocarbon groups carrying a 1-oxo substituent. It will also be appreciated that the term 'thioester' includes ester groups derived from dithiocarbonic acids (xanthate group), as well as acylthio groups derived from thiocarboxylic acids.

The compounds of the invention may possess substituents at other positions of the steriod nucleus, for example at the 2, $3\beta$, 11 or $16\alpha$ positions. They may also be unsaturated, for example at the $\Delta^{8(9)}$ and/or $\Delta^1$ and $\Delta^4$ positions.

In general, the compounds of the invention are good anaesthetics with generally short induction periods, the anaesthetic action at suitable doses being in general instantaneous; these compounds are thus excellent anaesthetics for inducing anaesthesia which is to be maintained e.g. by an inhalation anaesthetic such as ether, halothane, nitrous oxide, or trichloroethylene. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side effects as compared to many previously described steroidal anaeshtetics.

The esterified carboxyl groups which may be present in the above 21-substituents are preferably alkoxycarbonyl groups.

In general, alkyl, alkenyl, alkoxy, alkanoyl and alkoxycarbonyl groups referred to herein with reference to the 21-position may have 1–6 carbon atoms and may be unsubstituted or substituted.

Acyl groups may in general be alkanoyl, aroyl or aralkanoyl groups, the aromatic portions of which latter groups being preferably monocyclic and either carbocyclic or heterocyclic. Such groups may be unsubstituted or substituted e.g. by the N-attached residues referred to above or by carboxylic acid groups. Heterocyclic aromatic groups may for example have 5 or 6 ring members and there may be one or more hetero atoms e.g. nitrogen.

Thioether groups may for example be groups of the formula $-SR^8$ were $R^8$ is an alkyl, alkenyl, alkynyl, aralkyl, aralkenyl or aralkynyl group or a carbon-attached heterocyclic group. The alkyl groups may be substituted for example by an N-attached residue such as referred to above and particularly an N-attached residue of a heterocyclic amine. The heterocyclic groups may be saturated or unsaturated and contain 5 and 6 ring members. They are preferably monocyclic and contain nitrogen; a second hetero atom (e.g. nitrogen) may be present. Examples of such groups are pyrid-2-yl and pyrimid-2-yl.

Thioester groups may for example be acylthio groups of the formula $-SCO.R^9$ where $R^9$ is a substituted or unsubstituted alkyl group (which may be substituted for example by an N-attached residue referred to above and particularly an N-attached residue of a heterocyclic amine), alkenyl, alkynyl, aryl, aralkyl, aralkenyl or aralkynyl group or a carbon-attached heterocyclic group such as just described (e.g. pyrid-3-yl).

Alternatively, the thioester group may be a xanthate group of the formula —SCS.OR$^{10}$ where R$^{10}$ is an alkyl group substituted by an N-attached residue such as referred to above particularly the N-attached residue of a dialkyl- or heterocyclic amine.

The N-attached residues referred to above may for example, be groups of the formula —NR$^6$R$^7$ where R$^6$ and R$^7$ taken together with the nitrogen atom represent a saturated or unsaturated, substituted or unsubstituted 3-8, preferably 5 or 6, membered ring which may contain one or more further hetero atoms such as nitrogen, oxygen or sulphur. Such rings may be substituted for example by one or more alkyl (e.g. methyl), aralkyl (e.g. benzyl), oxo, alkoxy, alkoxycarbonyl or acyloxy groups; the rings may also be fused to a benzene ring (e.g. phthalimido).

Preferred examples of such N-attached residues, on account of their superior activity, are a morpholino group (which may be substituted by one or more methyl groups) or a thiamorpholino, thiazolidino, phthalimido or piperidino group.

Alternatively, the N-attached residue may be a group of the formula —NR$^6$R$^7$ in which R$^6$ and R$^7$ which may be the same or different are each a hydrogen atom, a substituted or unsubstituted alkyl, alkenyl, aralkyl or aryl group or an acyl group. The alkyl groups may have 1 to 6 carbon atoms (e.g. methyl or ethyl) and may for example be substituted by an oxo, a hydroxy, alkoxy or acyloxy group.

When R$^2$ is an alkyl group, the alkyl group perferably has 1-6 carbon atoms e.g. methyl, ethyl or n-butyl. When R$^2$ is substituted by an N-attached residue as referred to above or an hydroxy, alkoxy, acyloxy, thioether or thioester group or a chlorine or fluorine atom, it is preferably a methyl group. The N-attached residue should in this case be a residue of a heterocyclic amine such as described above, although compounds having alkyl groups substituted by other N-attached residues are useful as intermediates in the preparation of compounds in accordance with the invention.

When R$^2$ is a formyl group, the compound is preferably in the form of a dialkyl (for example C$_{1-3}$ e.g. methyl) acetal, a cyclic (alkylene e.g. C$_{2-4}$) acetal or a 20-alkyl (e.g. C$_{1-4}$, preferably methyl) enol ether.

Where R$^2$ is an alkoxymethyl or alkylthiomethyl group, the alkoxy or alkylthio portion of R$^2$ conveniently has 1-6 carbon atoms, e.g. methoxy, ethoxy and ethylthio and it may be substituted e.g. by a substituent such as described for R$^5$ below.

When R$^2$ is an acyloxymethyl or acylthiomethyl group, the acyl portion R$^2$ is conveniently a group of the formula —CO.R$^5$ where R$^5$ is an alkyl (C$_{1-5}$), phenyl or benzyl group. Examples of such alkyl groups are methyl and ethyl. R$^5$ may be substituted by an N-attached residue such as referred to above, and examples of such substituents include amino, methylamino, dimethylamino, ethylamino, diethylamino and, preferably, morpholino or thiamorpholino. A morpholino substituent may itself be substituted, e.g. by C$_{1-6}$ alkyl groups e.g. one or more methyl groups. Alternatively R$^5$ may be substituted by a halogen (e.g. chlorine atom) or a carboxylic acid group, e.g. when R$^2$ is a hemisuccinyloxy group.

When R$^2$ is an alkoxycarbonyl group, the alkyl portion of R$^2$ conveniently has 1-4 carbon atoms e.g. methyl and ethyl and thus may also, if desired, carry an N-attached residue as described above for R$^5$.

Where R$^2$ is an acyl group, it is conveniently an alkanoyl group, the alkyl portion of which contains 1-5 carbon atoms, e.g. methyl, ethyl and propyl. Alternatively, R$^2$ may be a heterocyclic aroyl group, such as a pyridinecarbonyl group. In general the alkyl portions of the alkanoyl groups may be substituted, e.g. by the substituents referred to above for R$^5$ groups.

Where R$^2$ is a group of the formula I or II as referred to above, R$^3$ and R$^4$ are conveniently alkyl or alkoxy groups containing 1-4 carbon atoms, preferably methyl or ethoxy. The alkyl portions of such groups may be substituted, for example, by the N-attached residues referred to above.

Preferably, the whole group of formula I contains more than 5 carbon atoms.

Where R$^1$ and R$^2$ are both alkyl groups the groups are conveniently the same and are preferably methyl groups.

When R$^1$ and R$^2$ taken together represent an alkylidene group, it is conveniently a methylene group. Such compounds are of particular interest.

The compounds of the invention which are generally preferred on account of their generally superior anaesthetic properties are those in which R$^1$ is a hydrogen atom and R$^2$ is an alkyl, alkoxycarbonyl, alkoxymethyl, chloromethyl, acyloxymethyl, acylthiomethyl, C-attached heterocyclic aryl thiomethyl or alkylthiomethyl group or an aminomethyl group (in which the amino group is the N-attached residue of a heterocyclic amine) and the enol ethers and acetals of compounds where R$^2$ is a formyl group; compounds wherein both R$^1$ and R$^2$ are alkyl groups; and compounds having a 20-cyclopropyl group.

Compounds in the pregnane series are also generally preferred, as are compounds having an 11-oxo group.

Examples of substituents which may be present at the 2β-position include an acyloxy group having for example 1 to 9 carbon atoms, an ether or thioether group (i.e. the residue of an alcohol, a phenol or a thiol) containing for example 1-9 carbon atoms (e.g. methoxy), an alkyl or cycloalkyl group for example containing up to 9 carbon atoms, an aryl group (e.g. a phenyl group), an aralkyl group (e.g. a benzyl group), a hydroxy group, a thiocyanato group, a nitro-oxy group, or a halogen atom.

Acyloxy substituents (which may be saturated or unsaturated) include lower (C$_1$–C$_6$) alkanoyloxy groups, (substituted if desired, for example, with one or more halogen, e.g. chlorine atoms, lower alkoxy, amino or substituted amino groups), aroyloxy groups (e.g. a benzoyloxy group), or aralkanoyloxy groups (e.g. a phenylacetoxy group).

Ether substituents, which may be saturated or unsaturated, include lower (C$_1$–C$_6$) alkoxy groups, lower alkenyloxy groups (e.g. an allyloxy group), cycloalkoxy groups (e.g. a cyclohexyloxy group), aryloxy groups (e.g. a phenoxy group) and aralkoxy groups (e.g. a benzyloxy group). Thioether groups corresponding to the above-mentioned ether groups are representative of 2β-thioether substituents.

The 2β-substituent may alternatively be an azido, sulphonyloxy (e.g. tosyloxy) group or an acylthio group.

Examples of 2β-alkyl groups include especially lower alkyl groups containing 1–5 carbon atoms such as methyl, ethyl, propyl, butyl, isobutyl and t-butyl groups. An example of a cycloalkyl group is a cyclohexyl group Examples of lower alkanoyloxy 2β-substituents include acetoxy, propionyloxy, butyryloxy piperidinoacetoxy, morpholinoacetoxy, diethylaminoacetoxy and chloroacetoxy groups. Examples of lower alkoxy groups include methoxy, ethoxy, propoxy, isopropoxy, n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino (e.g. morpholino) groups, or substituted or unsubstituted acyloxy (e.g. morpholinoacetoxy, chloroacetoxy or diethylaminoacetoxy), or heterocyclic groups, e.g. a tetrahydrofuranyl group. Alkyl, cycloalkyl and aryl groups may also be substituted.

The 2β-position may also carry amino substituents, e.g. amino or substituted amino groups, for example mono- or di-alkylamino or saturated, unsaturated or aromatic heterocyclic amino groups, e.g. a morpholino group.

A particularly important 2β-substituent is an ethoxy group.

Examples of substituents which may be present at the 2α-position are alkyl groups, e.g. having 1 to 6 carbon atoms such as methyl or ethyl, or halogen atoms, e.g. chlorine or bromine.

Examples of substituents which may be present at the 3β-position are alkyl groups, e.g. having 1 to 6 carbon atoms such as methyl, ethyl or pentyl.

An oxo group may be present at the 11-position and compounds having this substituent are particularly important. Alternatively, a hydroxy group may be present at the 11-position, in either the α configuration or, in the presence or absence of an α-alkyl or alkenyl ($C_{1-6}$) group (e.g. methyl or allyl), in the β configuration. Another possible grouping is in an epoxy group linked also to the 9-position.

The 16-position may be substituted for example by a methyl, ethyl or methoxy group or by a halogen atom (e.g. fluorine or chlorine).

Certain of the compounds of the invention, e.g. those containing a basic nitrogen atom, are capable of forming acid addition salts and this has the advantage of tending to improve the water solubility of the compounds. Such salts include, in the case of amino-substituted compounds, hydrochlorides, hydrobromides, phosphates, sulphates, p-toluenesulphonates, methanesulphonates, citrates, tartrates, acetates, ascorbates, lactates, maleates and succinates.

Compounds having an acidic group are capable of forming water soluble salts, such as alkali metal, e.g. sodium, potassium or lithium, and ammonium (including substituted ammonium) salts.

When these salts are used as anaesthetics they should be non-toxic, i.e. physiologically acceptable in the dosage at which they are administered. Other salts may, however, be of use in for example, isolation of the product from a synthetic reaction.

Particularly preferred compounds in accordance with the invention by virtue of their excellent anaesthetic properties are:

1. 3α-Hydroxy-21-methyl-5α-pregnane-11,20-dione;
2. 3α-Hydroxy-21-n-butyl-5α-pregnane-11,20-dione;
3. 21-Ethoxycarbonyl-3α-hydroxy-5α-pregnane-11,20-dione;
4. 3α-Hydroxy-21-methoxycarbonyl-5α-pregnane-11,20-dione;
5. 21-Formyl-3α-hydroxy-20-methoxy-5α-pregn-20-en-11-one.
6. 21-Ethoxymethyl-3α-hydroxy-5α-pregnane-11,20-dione;
7. 3α-Hydroxy-21-methoxymethyl-5α-pregnane-11,20-dione;
8. 21,21-Dimethyl-3α-hydroxy-5αpregnane-11,20-dione;
9. 21,21-Ethylene-3α-hydroxy-5α-pregnane-11,20-dione;
10. 21-Ethyl-3α-hydroxy-5α-pregnane-11,20-dione;
11. 21-Chloromethyl-3α-hydroxy-5α-pregnane-11,20-dione;
12. 3α-Hydroxy-21-thiazolidinomethyl-5α-pregnane-11,20-dione and its salts;
13. 21-Acetoxymethyl-3α-hydroxy-5α-pregnane-11,20-dione;
14. 3α-Hydroxy-21-morpholinoacetoxymethyl-5α-pregnane-11,20-dione and its salts;
15. 3α-Hydroxy-21-phthalimidomethyl-5α-pregnane-11,20,-dione;
16. 3α-Hydroxy-21-morpholinoacetylthio-5α-pregnane-11,20,-dione.
17. 3αHydroxy-21-(pyrid-2-ylthiomethyl)-5α-pregnane-11,20-dione; and
18. 3α-Hydroxy-21-(pyrid-3-yl-carbonylthiomethyl)-5α-pregnane-11,20-dione.

PHARMACEUTICAL FORMULATIONS

The anaesthetic compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises an anaesthetic composition for parenteral administration comprising an anaesthetic compound in accordance with the invention in a parenterally acceptable vehicle.

When the anaesthetic compounds are sufficiently soluble in water (e.g. the salts, particularly the citrates referred to above) they may be formulated in aqueous solutions (e.g. isotonic sterile solutions). Many of the anaesthetic steroids of the invention are poorly soluble in water. We have found however that they may be formulated for parenteral administration in an aqueous solution of a parenterally acceptable non-ionic surface active agent. These surface active agents may also be used even where the steroid is sufficiently water soluble as they may reduce the risk of thrombo-phlebitis.

The non-ionic surface active agents used for the purpose of this invention are generally those of the water-soluble type, conveniently having an HLB value of at least 9, preferably at least about 12, advantageously at least about 13. Preferably the HLB value of the surface active agent is not greater than about 18. A mixture of surface agents may be used, in which case it is the HLB value of the mixture which is conveniently between the values just mentioned.

The surface active agent must naturally be one which is physiologically compatible, i.e. of itself give rise to no physiologically unacceptable side effects in the dosages employed in the intended species to be treated (man or animal).

Surface active agents for use in accordance with the invention are for example to be found among the following non-ionic surfactants and classes of surfactants:

Polyoxyethylated derivatives of fatty (C12–C20) glyceride oils, e.g. castor oil, containing from 35 to 60 oxyethylene groups per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 5 to 150 and from 15 to 50 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12–18) esters of sugar alcohol anhydrides e.g. sorbitan or mannitan.

Long-chain (e.g. C10–16) alkanoyl mono- and di-alkanolamides (the alkanol portions of which for example contain 1–5 carbon atoms) for example lauroyl mono- and di-ethanolamides. Polyethylene glycol esters (containing from 6 to 40 ethylene oxide units) of long chain fatty acids (containing for example 12–18 carbon atoms) e.g. polyethyleneglycol monooleate (containing for example 8 ethylene oxide units).

Other useful surfactants include phospholipids such as lecithins, e.g. egg or soyabean lecithins.

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monostearate containing about 20 ethylene oxide units; and Tween 40, polyoxyethylene sorbitan monopalmitate containing about 20 ethylene oxide units.

The expression "solutions" is used herein to denote liquids which have the appearance of true solutions and are thus optically clear and capable of passage, for example, through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injection.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

In one method of preparing the solutions comprising a surfactant, the steroid is first dissolved in the selected surfactant, for example with heating, and the resulting solution dissolved in water. Alternatively the steroid may be dissolved in a volatile organic solvent advantageously having a boiling point of less than about 80 C which is miscible with the surface active agent such as a volatile lower aliphatic ketone e.g. acetone or methyl ethyl ketone or a volatile halogenated hydrocarbon e.g. chloroform or methylene chloride. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steriod with an aqueous solution of the surface active agent.

In all cases simple tests enable one to determine the relative proportions of surface active agent required.

As will be clear, the proportion of steroid which is dissolved in the aqueous medium according to the invention depends upon the water-solubility of the steroid and, where present, the nature and amount of surface active agent used. The composition will generally contain at least 1 mg/ml of steroid but solutions can be made containing for example up to 7 mg/ml of steroid or even 10 mg/ml.

Where the compounds carry salt forming groups, higher concentrations may be achieved, e.g. up to 100 mg/ml.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.2 to 30 mg/kg will in general be found to be satisfactory to induce anaesthesia, the preferred dose being within the range of from 0.5 to 20 mg/kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of about 0.025–2.0 (e.g. 0.09–1.4) mg/kg min.

Where the anaesthetic solutions are administered intramuscularly, higher doses are generally necessary.

COMPOUND PREPARATION

The compounds of the invention may be prepared by any convenient method, for example one of those given below.

In these preparations it is often necessary to protect the 3-hydroxy group and thus the final step of the reaction is often the regeneration of this group as is described hereinafter.

Compounds wherein $R^1$ is a hydrogen atom and $R^2$ is an alkyl group may be prepared from corresponding 20,21-epoxy pregnanes by reaction with a compound furnishing an anion ($R^2$) and a cation, followed, where a metal derivative of the 20-hydroxy group is first formed, by treatment with a source of protons, e.g. water, to regenerate the hydroxy group, which is then oxidised to the required 20-oxo group.

This method may conveniently be carried out with a metal alkyl, particularly a lithium dialkyl cuprate, to yield in the first instance a 21-alkyl, 20-hydroxy pregnane. This reaction is desirably carried out at low temperatures, e.g. below ambient temperatures, e.g. 0° C, and in a variety of inert solvents, e.g. an ether solvent such as tetrahydrofuran, dioxan or diethyl ether.

It is desirable to protect the 3α-hdyroxy group during this reaction, e.g. as an ester, such as a nitrate or acetate, or an ether, such as a tetrahydropyranyl ether.

The 21-alkyl, 20-hydroxy compound may then be oxidised, conveniently with potassium dichromate/sulphuric acid/acetone, to the corresponding 20-oxo compound. In some cases, the oxidation conditions will effect removal of the protecting group from the 3α-hydroxy group which will then be oxidised to a 3-keto group; the desired 3α-hydroxy compound may however be regenerated by stereospecific reduction. This latter step may be carried out by the method of Browne & Kirk (J. Chem. Soc. C, 1969, 1653), or, conveniently, by the method described in our copending British Pat. No. 52465/71 (A14), which is referred to in more detail below.

Compounds wherein $R^1$ is a hydrogen atom and $R^2$ is an alkyl group may also be prepared by reacting a corresponding 21-alkylidene (e.g. 21-methylene) compound with a metal alkyl (e.g. by reaction with a lithium dialkyl cuprate under conditions such as described above).

Compounds wherein $R^1$ is a hydrogen atom and $R^2$ is an alkyl group substituted by an N-attached residue of a primary or secondary amine or ammonia may be prepared by a Mannich reaction between the corresponding 21-unsubstituted pregnane, the amine or ammonia and an aldehyde. The aldehyde may generally have up to 6 carbon atoms and be saturated, but formaldehyde is preferably used, conveniently in the form of paraformaldehyde. The reaction is preferably carried out in a relatively high boiling solvent, for example a carboxylic acid such as acetic or propionic acid, or an alcohol such as isoamyl alcohol; or an ether solvent such as tetrahydrofuran or dimethoxyethane, at any suitable temperature up to reflux, preferably at an elevated temperature e.g. 90°–110° C. The reaction is desirably carried out in the presence of an acid, e.g. hydrochloric acid or p-toluenesulphonic acid.

If the Mannich condensation is effected under forcing conditions, for example for a prolonged time (e.g. about 4 times the reaction time for optimal yield of the initial Mannich reaction) at a relatively high temperature, a 21-alkylidene-21-aminoalkyl (or substituted aminoalkyl) derivative is obtained.

Compounds wherein $R^1$ is a hydrogen atom and $R^2$ is an alkyl group substituted by an N-attached residue of a primary or secondary amine or ammonia may also be prepared by the reaction of the 21-alkylidene compound with the appropriate amine or ammonia in an inert solvent, for example, an ether solvent such as tetrahydrofuran. The amine may also be used as solvent for the reaction. The reaction may be effected at a temperature of 0-100° conveniently at ambient temperature. The method is particularly useful since only small quantities of the amino reagent are used in the preparation, for example, in the preparation of the thiazolidinomethyl compounds.

Compounds wherein $R^1$ and $R^2$ taken together represent an alkylidene group (e.g. methylene group) may be prepared from a corresponding Mannich base having a 21-amino- or -substituted aminoalkyl group, especially a substituted methyl group, by a Hoffmann elimination i.e. by quaternising the amino group, for example with an alkyl halide such as methyl iodide followed by decomposition of the quaternary salt so formed. The elimination reaction may be carried out by refluxing the quanternary compound in a polar solvent, e.g. an alkanol such as ethanol. Such 21-alkylidene compounds can be reduced, e.g. by catalytic hydrogenation, to the corresponding 21-alkyl compounds.

Compounds wherein $R^1$ is a hydrogen atom and $R^2$ is a formyl group may be prepared by a Claisen condensation between the corresponding 21-unsubstituted compound and an alkyl (e.g. ethyl) formate. This reaction may be carried out in a solvent, preferably a polar solvent such as dimethylsulphoxide, and in the presence of a base, such as an alkali metal (e.g. sodium) or an alkali metal hydride (e.g. sodium hydride). The 3α-hydroxy group may be protected during the reaction to avoid the formation of 3α-esters conveniently as the tetrahydropyranyl ether. When it is necessary to regenerate the hydroxy group as the last step of the reaction, this may be done directly in the usual way by hydrolysis, for example acidic hydrolysis. However, it is preferable first to form a dialkyl (e.g. dimethyl) acetal while at the same time regenerating the 3α-hydroxy group and then to regenerate the formyl group.

The acetals of the invention may be prepared by reacting the corresponding 21-formyl compound with an alkanol e.g. ethanol or methanol or diol e.g. ethylene glycol. This reaction is desirably carried out in the presence of a strong acid, e.g. perchloric or hydrochloric acid. The alcohol conveniently acts as the reaction solvent, and the reaction may be carried out at ambient temperature. Where the 3α-hydroxy group is protected as an acid labile group, it is regenerated in the course of this reaction. A 21- formyl group may be introduced or re-introduced by splitting such acetals under mild conditions, e.g. by heating the acetal in a weak acid medium (e.g. aqueous acetic acid) at a moderate temperature, such as 50°–80° C.

Compounds wherein $R^1$ is a hydrogen atom and $R^2$ is a hydroxymethyl group may be prepared by selectively reducing a corresponding 21-formyl compound, e.g. as described in our copending British Pat. No. 52465/71 (A 14) referred to hereinafter. In this reaction the 3α-hydroxy group may conveniently be protected, in which case it is subsequently regenerated when the reduction is complete.

Compounds wherein $R^1$ is a hydrogen atom and $R^2$ is an acyloxy alkyl group may be prepared by acylation of a corresponding 21-hydroxyalkyl compound. The acylation is conveniently carried out with a carboxylic acid or a reactive derivative thereof such as an acid halide (e.g. chloride), ester or anhydride. The acylating agent is preferably an acid halide or anhydride and the reaction carried out in the presence of an acid binding agent such as pyridine or triethylamine. If the 21-hydroxyalkyl steroid is initially obtained in a form carrying a protected 3α-hydroxy group, the esterification may be effected before selective removal of the protecting group.

Compounds wherein $R^1$ is a hydrogen atom and $R^2$ is an alkanoyloxy alkyl group substituted by an amino group may for example be prepared by reacting an amine with the corresponding iodoalkanoyloxyalkyl (e.g. iodoacetoxymethyl) group. The iodo compound required for this reaction may for example be prepared by reacting the corresponding chloroalkanoyloxyalkyl compound with an alkali metal (e.g. sodium) iodide.

Compounds wherein $R^1$ is a hydrogen atom and $R^2$ is an ether- or thioether- substituted alkyl group (e.g. an alkoxyalkyl or alkylthioalkyl group) may be prepared from a corresponding 21-alkylidene compound by reaction with an alcohol (e.g. alkanol) or thiol corresponding to the desired ether or thioether group. The reaction may be accelerated by either an acid or base catalyst, conveniently a base such as an alkali metal bicarbonate e.g. potassium bicarbonate. In the case of alkoxy derivatives, the solvent is conveniently the alkanol itself, whereas in the case of alkylthio derivatives the solvent may be the thiol (where liquid) or a different solvent such as acetone. The reaction may be carried out at any suitable temperature up to (and preferably at) reflux.

Compounds wherein $R^1$ is hydrogen and $R^2$ is a thioester- substituted alkyl group such as acylthioalkyl (e.g. acylthiomethyl) or alkoxycarbodithioalkyl group may similarly be prepared by reacting the corresponding 21-alkylidene (e.g. 21-methylene) compound with a thio acid (e.g. $R^9COSH$ or $R^{10}O.CS.SH$) in a solvent such as acetone. The reaction is conveniently carried out at reflux. In certain cases (e.g. when the acid is thioacetic acid) the acid itself may act as solvent and the reaction may be performed at room temperature.

Compounds having a 21-fluoromethyl or chloromethyl group may be prepared by reacting dry HF or HCl with the 21-methylene compound in an inert solvent (e.g. an ether such as dioxan).

Compounds wherein $R^1$ is a hydrogen atom and $R^2$ is an alkyl (e.g. methyl) group substituted by a phthalimido group may be prepared by reacting a corresponding haloalkyl (e.g. chloromethyl) compound with an alkali metal (e.g. potassium) phthalimide. The reaction is may be carried out in a solvent such as acetone, at any temperature up to and preferably at reflux.

Compounds wherein $R^1$ is a hydrogen atom and $R^2$ is an esterified carboxyl (e.g. alkoxycarbonyl) group may be prepared by a Claisen condensation reaction between a corresponding 21-unsubstituted compound and a diester of carbonic acid (e.g. a dialkyl, such as diethyl carbonate). The reaction is desirably carried out in the presence of a strong base (e.g. as described above with reference to the introduction of a 21-formyl group) such as sodium hydride. It may be carried out in a solvent, conveniently the dialkyl carbonate itself, at any suitable temperature up to and preferably at reflux. It is necessary to protect the $3\alpha$-hydroxy group during this reaction e.g. by the methods referred to above, conveniently as the tetrahydropyranyl ether. In the above Claisen reaction the dialkyl carbonate is most conveniently diethyl carbonate, and it is then convenient to prepare other 21-esterified carboxyl compounds from the so-formed ethoxycarbonyl compound, by transesterification with an alcohol (e.g. an alkanol corresponding to a desired alkoxy group), desirably in the presence of a base, e.g. an alkali metal bicarbonate such as potassium bicarbonate. The alcohol conveniently acts as the reaction solvent and any suitable temperature up to and preferably at reflux may be used. The reaction is advantageously carried out under an inert (e.g. nitrogen) atmosphere.

Compounds wherein $R^1$ is a hydrogen atom and $R^2$ is an acyl group may be prepared by a Claisen condensation between the corresponding 21-unsubstituted compound and an ester such as a $C_{1-6}$ alkyl (e.g. ethyl) ester, of the corresponding carboxylic acid; the latter may act as the reaction solvent. Generally, however, the solvent may be a polar solvent such as an alcohol, e.g. ethanol or a sulphoxide solvent such as dimethyl sulphoxide.

The reaction is conveniently carried out at ambient temperatures, desirably in the presence of a strong base, particularly an alkali metal hydride such as sodium hydride or an alkali metal alkoxide such as sodium alkoxide. It is not necessary, but is may be convenient, for the $3\alpha$-hydroxy group to be protected during this reaction.

Further compounds according to the invention may be prepared from a steroid having a readily eliminatable 21-substituent e.g. a 21-halo (e.g. bromo or chloro) or alkylsulphonyl (e.g. methyl sulphonyl) or aryl sulphonyl (e.g. p-toluenesulphonyl) compound by nucleophilic displacement reactions with compounds generating carbanions. Thus, for example, compounds wherein $R^1$ is a hydrogen atom and $R^2$ is a group of the formula I may be prepared by reacting such a 21-substituted (e.g. bromo) compound with a compound of the formula

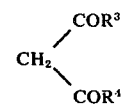

where $R^3$ and $R^4$ are as defined above or a reactive derivative thereof such as an alkali metal, e.g. sodio derivative. This reaction may be carried out under conditions conventional for reactive methine condensations i.e. in the presence of a strong base such as an alkali metal (e.g. sodium) or a hydride or alkoxide thereof in a polar solvent, preferably an alkanol solvent such as ethanol. This reaction is conveniently carried out at room temperature.

Compounds wherein $R^1$ is a hydrogen atom and $R^2$ is a group of the formula II may be prepared by reaction of a corresponding compound having a 21-methylene group with a compound of the formula

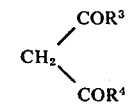

where $R^3$ and $R^4$ are as defined above, under reaction conditions similar to those just described for the preparation of compounds wherein $R^2$ is a group of the formula I.

Compounds wherein both $R^1$ and $R^2$ are alkyl groups may be prepared by reducing a corresponding 21-(alkylidene), 21-(1'-amino- or substituted amino-alkyl) compound. The reduction is conveniently effected with hydrogen/palladium/carbon in an inert solvent, preferably an ester solvent such as ethyl acetate.

Compounds wherein both $R^1$ and $R^2$ are both esterified carboxyl groups may be prepared by reacting a reactive derivative of a corresponding androstane-17-carboxylic acid such as an acid halide, e.g. the chloride, with a compound of the formula

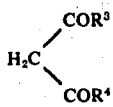

where $R^3$ and $R^4$ are alkoxy groups or a reactive derivative thereof, such as an alkali metal (e.g. sodio) derivative. The reaction may be carried out in an inert solvent such as an ether solvent such as tetrahydrofuran, at any suitable temperature up to and preferably at reflux. The reaction is desirably carried out in the presence of a strong base such as an alkali metal hydride e.g. sodium hydride; the separate addition of a base is not necessary when an alkali metal derivative is used as the starting reagent.

It is necessary to protect the 3α-hydroxy group during this reaction, in an acid stable form, e.g. as a nitrate ester, from which the hydroxy group can be regenerated by reduction, e.g. with zinc in acetic acid.

The steroid starting material for this reaction may be prepared from the corresponding androstane 17β-carboxylic acid; for example, an androstane having a 17β-carbonyl halide group may be prepared by reacting the corresponding compound having a 17β-carboxylic acid group with an oxalyl halide (e.g. oxalyl chloride), conveniently in an ether solvent such as tetrahydrofuran.

Compounds wherein $R^1$ and $R^2$ taken together with the 21- carbon atom represent a cyclopropyl group or substituted cyclopropyl group may be prepared from a corresponding 21-alkylidene compound by reaction with a reactive methylide, such as dimethyl sulphoxonium methylide, conveniently in a sulphoxide solvent such as dimethylsulphoxide. The reaction may be carried out at ambient temperatures. The methylide reagent may conveniently be prepared in situ, for example from a trimethylsulphoxonium halide (e.g. iodide) in the sulphoxide solvent in the presence of a strong base such as an alkali metal (e.g. sodium) hydride.

The 20-alkyl enol ethers of compounds wherein $R^1$ is a hydrogen atom and $R^2$ is a formyl group may be prepared by reacting a 21-unsubstituted compound with a trialkyl (especially triethyl) orthoformate in the presence of a strong acid (e.g. perchloric acid). This reaction is desirably effected at below ambient temperatures (e.g. 0° C). The orthoformate may act as the reaction solvent.

The 3α-hydroxy group should be protected during this reaction in a form which is stable to acid and from which the hydroxy group can be regenerated by treatment with a base. It is conveniently protected in the form of an acetate ester, from which it can be regenerated with a weak base (e.g. an alkali metal bicarbonate such as potassium bicarbonate) in a polar solvent, e.g. an alkanol such as ethanol.

Analogous enol ethers may be similarly prepared, but are more conveniently prepared by transetherification of the 20-ethyl enol ether and an alkanol (e.g. methanol) corresponding to the desired alkoxy group.

The alkanol may act as the solvent for the reaction, which may be catalysed by a base such as potassium bicarbonate.

Acetals of compounds having a 21-formyl group may also be prepared from these 20-enol ethers by treating them with an alkanol in the presence of a strong acid such as perchloric acid.

In the preparation of compounds in accordance with the invention possessing an optional substituent or a carbon-carbon double bond such as described above, it is convenient for this substituent or unsaturation to be present in the 21-substituted starting material. Alternatively, these substituents or unsaturation may be introduced subsequently by generally known techniques using known compounds as starting materials. For convenience a number of methods of introducing the desired substituents or unsaturation into a 3-oxygenated-20-oxo-pregnane are set out below; certain of these methods are new.

Substitution at the 2β-position in the 5α- can be effected for example by way of the corresponding 2α, 3α-epoxy compound. The epoxy compound itself may be prepared by first dehydrating a 3α-hydroxy compound to give the corresponding $\Delta^2$ compound (e.g. by first tosylating the hydroxy group and then detosylating the product), and then treating the $\Delta^2$ compound with a peracid to form the 2α, 3αepoxide ring.

A 2βsubstituent may then be introduced by the method described in U.S. patent application Ser. No. 197,915. This general method may be used to introduce all the 2β-substituents described above.

Methods for introducing substituents at the 2α, 3β, 11 and 16α and positions are described in U.S. applications Ser. Nos. 208,959 (Part 13) and 194,918 (Part 6). These or analogous methods may be used to introduce all the substituents referred to above at these positions. For example, an 11-alkenyl or 16-alkyl group may be introduced by methods analogous to those described in U.S. patent application Ser. No. 208,959 for the introduction of an 11-allyl or 16-methyl substituent. 5α-Steroids possessing $\Delta^1$ unsaturation may also be prepared by known methods, but we prefer to use a method which comprises converting a 3α-bromo-3α-hydroxy pregnane into its corresponding 2β,21-dibromo compound, if desired protecting the 3α-hydroxy group (e.g. as its tetrahydropyranyl ether), dehydrobrominating to give the $\Delta^1$ compound, and then deprotecting the product where necessary to give the desired 1,2-dehydro-3α-hydroxy-20-oxo-21-bromo compound.

The dehydrobromination may be effected, for example using a nitrogen containing Lewis base such as a dilower alkly lower acylamide e.g. dimethylformamide or dimethylacetamide advantageously in the presence of an alkali metal or alkaline earth metal carbonate, for example calcium carbonate.

In general it has been found convenient to effect the dehydrobromination at an elevated temperature for example from 80° to 170° C. Lower temperatures may be employed with a lithium or calcium halide is present.

Compounds possessing $\Delta^4$ unsaturation may be prepared form $\Delta^3$-steroids by methods analogous to those described for obtaining the $\Delta^1$ compounds from $\Delta^2$ steroids. Alternatively, $\Delta^4$-steroids may be obtained by the methods described in U.S. patent application Ser. No. 194,918.

Compounds having a double bond between the 8-and 9-positions and an 11-oxo group may be prepared for example by the method described in U.S. patent application Ser. No. 208,959. These compounds may also be prepared by dehydration of the corresponding 9α-hydroxy compound, for example using thionyl chloride in pyridine.

5α-Steroids of the invention may also be prepared from the corresponding 3-oxo compounds by stereo-specific reduction, e.g. by the method of *Browne and Kirk* (J. Chem. Soc. C, 1969, 1653) or by the method of U.S. patent application Ser. No. 305,246 (A 14). The latter method preferably uses a pre-formed iridium catalyst reduction system. For example, a reduction system may be prepared from an iridium acid or salt (e.g. chloroiridic acid), trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system if preformed by heating at reflux for 16 to 72 hours, the reduction can be accomplished in 2-3 hours at reflux; longer times may be necessary at room temperature.

In the preparative methods described above, it may be desirable to protect a 3α-hydroxy or 20-oxo group during the reaction, the protection being subsequently removed to regenerate the hydroxy or oxo group. A 3α-hydroxy group may for example be protected in the form of a nitrate ester or a tetrahydropyranyl ether. A 20-oxo group may be protected as a ketal and regenerated for example by hydrolysis in the presence of an acid (e.g. hydrochloric or acetic) at a temperature of 0°–100° C.

The invention is illustrated by the following Examples.

Optical rotations were determined in chloroform solution at ca. 0.5% concentration unless stated otherwise. Ultraviolet spectra were determined in ethanol. Temperatures are in °C. Melting points were measured in capillary tubes and are uncorrected. Preparative layer chromatography "preparative t.l.c." was carried out on silica gel. 'Petrol' refers to petroleum spirit (b.p. 60–80°). 'IMS' refers to industrial methylated spirits.

"Stock" chloroiridic acid solution was prepared by refluxing a mixture of chloroiridic acid (0.9 g.), 90% iso propyl alcohol (200 ml.) and trimethylphosphite (16 ml.) for 16 hr. The solution was neutralised with triethylamine immediately prior to use.

EXAMPLE 1

3α-Hydroxy-21-methyl-5α-pregnane-11,20-dione

21-Methyl-5α-pregnane-3,11,20-trione (0.4 g.) was added to "stock" chloroiridic acid solution (75 ml.) and the resulting mixture was refluxed for 2 hr. The solution was then cooled and partitioned between water and ether. The organic layer was washed with saturated aqueous sodium bicarbonate, dried ($Na_2SO_4$) and evaporated.

Recrystallisation of the residue from acetone/petrol gave title compound (365 mg.) as white prisms, m.p. 117°; $[\alpha]_D$ + 78° (c 1.0).

EXAMPLE 2

3α-Hydroxy-21-propionyl-5α-pregnane-11,20-dione

Ethyl propionate (0.5 ml) was added to a mixture of 3α-(tetrahydropyran-2ξ-yloxy)-5α-pregnane-11,20-dione (840 mg) and sodium hydride (130 mg) in dry dimethyl sulphoxide (15 ml.). The mixture was stirred, under $N_2$, for 2¼ hours then treated with methyl alcohol to destroy excess sodium hydride, and poured into 2N-hydrochloric acid. The precipitate was collected, washed and dried (884 mg.).

A solution of this product in ethyl alcohol (15 ml.) was treated with 2N-hydrochloric acid (1.5 ml.) and the mixture was stirred for 2 hrs., then poured into water. The product was extracted with ethyl acetate and the combined extracts were washed with water, dried and evaporated. Preparative t.l.c. of the residue (764 mg.) gave two fractions. The more polar fraction, after crystallisation from ethyl acetate/petrol gave title compound (239 mg.) m.p. 128°–130°, $[\alpha]_D$ + 79.2°, $\lambda_{max}$. 277.5 nm (ε 12,700).

EXAMPLE 3

3α-Hydroxy-21-picolinyl-5α-pregnane-11,20-dione

Ethyl picolinate (1.0 ml.) was added to a mixture of 3α-(tetrahydropyran-2ξ-yloxy)-5α-pregnane-11,20-dione (840 mg) and sodium hydride (130 mg.) in dry dimethyl sulphoxide (15 ml.). The mixture was stirred, under $N_2$, for ½ hr., then treated with methanol and poured into 2N-hydrochloric acid. The precipitate was collected, washed and dried to give 21-picolinyl-3α-(tetrahydropyran-2ξ-yloxy)-5α-pregnane-11,20-dione (695 mg.).

A solution of the tetrahydropyranyl derivative in ethyl alcohol (10 ml.) was treated with 2N-hydrochloric acid (1.0 ml.) and the mixture was stirred for 3 hours. The reaction mixture was poured into water and the product was extracted with ethyl acetate. The combined extracts were washed with water, dried and evaporated. The residue (684 mg.) was purified by preparative t.l.c. and crystallisation from ethyl acetate/petrol to give title compound (282 mg.) m.p. 179°–180°, $[\alpha]_D$ + 21.4°, $\lambda_{max}$. 236.5 nm (ε 6,600) $\lambda_{max}$. 316 nm (ε 17,630).

EXAMPLE 4

21-n-Butyl-3α-hydroxy-5α-pregnane-11,20-dione

A solution of 20β,21-epoxy-3α-hydroxy-5α-pregnan-11-one-3-nitrate (2.0 g) in dry ether (300 ml.) was added to a solution of lithium di-n-butyl cuprate in ether prepared by adding a solution of n-butyl lithium (31 ml. of 2 M solution) in hexane to a stirred slurry of cuprous iodide (6.0 g.) in dry ether (100 ml.) under nitrogen at −20°. The resulting mixture was stoppered and left at 0° for 2 days, and then partitioned between ethyl acetate and saturated aqueous ammonium chloride. The organic layer was washed with water, dried and evaporated.

A solution of the residue (2.4 g.) in acetone (165 ml.) was treated with a solution of potassium dichromate (4.8 g.) in 2N-sulphuric acid (42.5 ml.) at room temperature for 30 min. The mixture was then partitioned between water and ether and the organic layer was washed with water, dried and evaporated. The residue was subjected to preparative t.l.c.($CHCl_3$) to give crude 21-n-butyl-5α-pregnane-3, 11,20-trione (1.2 g.).

This foam was treated with "stock" chloroiridic solution (36 ml.) and refluxed for 8 hr. and then partitioned between water and ether. The organic layer was washed successively with saturated aqueous sodium bicarbonate, water and dried. Evaporation of the solvents afforded an oil which was purified by preparative t.l.c. EtOAc/petrol, 1:2; to give title compound (0.78 g.), as an oil; $[\alpha]_D + 95°$ (c 0.9).

EXAMPLE 5

21-Acetyl-3α-hydroxy-5α-pregnane-11,20-dione

A stirred solution of 3α-hydroxy-5α-pregnane-11,20-dione (1.0 g.) in dry ethyl acetate (15 ml.) was treated with sodium hydride (0.35 g.) under a nitrogen atmosphere. The mixture was then heated under reflux for 5 minutes, cooled and ethanol (1 ml.) was added to destroy excess sodium hydride. The product was extracted into ethyl acetate, washed with 2N, hydrochloric acid and then water. The organic layer was dried and evaporated. The residue (1.4 g.) was subjected to preparative t.l.c. (acetone/petrol 2:1) to give two fractions. One fraction, after trituration with ether, afforded 3α-acetoxy-21-acetyl-5α-pregnane-11,20-dione (0.5 g.), m.p. 155°–159°.

The second fraction (0.237 g.) after trituration with ether/petrol and then recrystallisation from ether gave the title compound (0.078 g.), m.p. 159°–161°, $[\alpha]_D + 74°$, $\lambda_{max}$. 276.5 nm ($\epsilon$ 13,000). Base added $\lambda_{max}$. 297.5nm($\epsilon$ 24,500).

EXAMPLE 6

21-Butyryl-3α-hydroxy-5α-pregnane-11,20-dione

Ethyl butyrate (0.84 ml) was added to a mixture of 3α-hydroxy-5α-pregnane-11,20-dione (665 mg) and sodium hydride (150 mg.) in dry dimethyl sulphoxide (10 ml.). The mixture was stirred, under $N_2$, for 1¾ hrs. The reaction mixture was treated with methyl alcohol to destroy excess sodium hydride, then poured into 2N-hydrochloric acid. The product was extracted with ethyl acetate and the combined extracts were washed with water, dried and evaporated. Preparative t.l.c. of the residue (859 mg.) gave two fractions. The more polar fraction was title compound (244 mg.) $[\alpha]_D + 74.0°$, $\lambda_{max}$. 278 nm ($\epsilon$ 12,980).

EXAMPLE 7

21,21-Diethoxycarbonyl-3α-hydroxy-5α-pregnane-11,20-dione

A solution of 3α-hydroxy-11-oxo-5α-androstane, 17β-carboxylic acid, 3-nitrate (0.44 g) in dry benzene (20 ml), oxalyl chloride (0.7 ml) and dry tetrahydrofuran (3 ml) was heated under reflux for 1½ hr. The solution was evaporated, redissolved in dry tetrahydrofuran and added to a solution of malonic ester (0.36 ml) and sodium hydride (0.06 g) in dry tetrahydrofuran (5 ml) under nitrogen and heated under reflux for ½ hr. The reaction mixture was cooled and poured into water. After acidification the mixture was extracted into chloroform and the extract washed with water dried (MgSO₄) and evaporated. The residue (0.81 g) was purified by preparative t.l.c. and this material (0.59 g) was dissolved in glacial acetic acid (15 ml) and treated with zinc (1.4 g). After ½ hr. the mixture was filtered and the filtrate extracted with chloroform. The extract was washed with water, dried MgSO₄) and evaporated. The residue (0.55 g) was purified by preparative t.l.c. and crystallisation from methyl acetate/petrol gave the title compound (0.27 g) m.p. 116°–117°, $[\alpha]_D + 45°$ (c, 0.75) $\lambda_{max}$. 258 nm ($\epsilon$ 7,500).

EXAMPLE 8

21-Diethoxycarbonylmethyl-3α-hydroxy-5α-pregnane-11,20-dione

A solution of sodium ethoxide, prepared from sodium (120 mg) and ethanol (20 ml), was treated with diethylmalonate (1 ml) and 21-bromo-3α-hydroxy-5α-pregnane-11,20-dione (500 mg) added to the solution. The mixture was stirred at room temperature for 7 hours, poured into water, and extracted into ethyl acetate. The extract was washed with water, dried (Na₂SO₄) and evaporated to a foam. Purification by preparative t.l.c. (ethyl acetate/petrol) gave title compound (180 mg) as a white foam $[\alpha]_D + 62.9°$ (c, 0.98).

EXAMPLE 9

21-(1'-Ethoxycarbonyl-2'-oxo-prop-1'-yl)-3α-hydroxy-5α-pregnane-11,20-dione

A solution of sodium ethoxide (7 ml - containing 70 mg of sodium) was treated with ethyl acetoacetate (1 ml) and 21-bromo-3α-hydroxy-5α-pregnane-11,20-dione (500 mg) added to the stirred solution. The resulting mixture was stirred at room temperature for 1 hour, poured into water, and extracted with ethyl acetate, the extract was washed with water, dried (Na₂SO₄) and evaporated to an oil which was purified by preparative t.l.c. (ethyl acetate/petrol) to give the title compound (210 mg) as a white foam $[\alpha]_D + 81.3°$ (c, 0.46).

EXAMPLE 10

21-(2',2'-Diacetylethyl)-3α-hydroxy-5α-pregnane-11,20-dione

A solution of sodium ethoxide, prepared from 120 mg of sodium in ethanol (20 ml), was treated with acetylacetone (1 ml) and the resulting solution added to a solution of 3α-hydroxy-21-methylene-5α-pregnane-11,20-dione (500 mg) in ethanol (20 ml). The mixture was stirred at room temperature for 1 hour, poured into water, and extracted into ether. The extract was washed with water, dried (Na₂SO₄) and evaporated to a white foam which was purified by preparative t.l.c. (ethyl acetate/petrol) to give title compound (480 mg) as a white foam $[\alpha]_D + 79.5$ °(c, 0.59).

EXAMPLE 11

21-(2'-Ethoxycarbonyl-3'-oxo-but-1'-yl)-3α-hydroxy-5α-pregnane-11,20-dione

A solution of sodium ethoxide (7 ml - containing 70 mg of sodium) was treated with ethyl acetoacetate (1 ml) and 3α-hydroxy-21-methylene-5α-pregnane-11,20-dione (500 mg) was added to the solution. The mixture was stirred at room temperature for 1 hour, poured into water, and extracted into ethyl acetate, the extract was washed with water, dried (Na₂SO₄) and evaporated to an oil which was purified by preparative t.l.c. (ethyl acetate/petrol) to give title compound (160 mg) as a foam, $[\alpha]_D + 74.1°$ (c, 0.84).

EXAMPLE 12

3α-Hydroxy-21-morpholinomethyl-5α-pregnane-11,20-dione

3α-Hydroxy-5α-pregnane-11,20-dione (1.0 g) in glacial acetic acid (20 ml.) was treated with morpholine (1.0 ml) and concentrated hydrochloric acid (1.0 ml). Paraformaldehyde (600 mg) was added to the stirred solution which was then heated in an oil-bath at 95°–100° for 1 hour. The solution was evaporated and dried in vacuo to a yellow oil (3.5 g.) which was partitioned between ethyl acetate and 0.1N hydrochloric acid. The colourless organic layer was extracted with more hydrochloric acid and the combined yellow aqueous layer was washed with ethyl acetate and basified with saturated sodium bicarbonate solution. The cloudy precipitate was extracted into ethyl acetate, and the extract washed with water, dried ($Na_2SO_4$) and evaporated to a pale yellow foam (1.05 g) which was purified by preparative t.l.c. in acetone to give title compound (534 mg) as a colourless foam, $[\alpha]_D + 73°$ (c, 0.81).

EXAMPLE 13

3α-Hydroxy-21-methylene-5α-pregnane-11,20-dione

3α-Hydroxy-21-morpholinomethyl-5α-pregnane-11,20-dione (500 mg) was added in small quantities to methyl iodide (2 ml) at 0° C. The solution was stirred at 0° C for 1 hour then at room temperature for 1 hour to give a waxy precipitate. The excess methyl iodide was washed away with benzene and the residue dried in vacuo to a yellow solid.

This solid was dissolved in ethanol and the solution refluxed for 24 hours, poured into water, and extracted with ethyl acetate, the extract was washed with water, dried ($Na_2SO_4$) and evaporated to a white foam which was purified by preparative t.l.c. (chloroform) to give a white foam (200 mg). Further purification by preparative t.l.c. in ethyl acetate/petrol gave a white foam (110 mg) which on crystallisation from hexane gave title compound (90 mg) as white needles, softening above 135° C., $[\alpha]_D + 168°$ (c, 0.16).

EXAMPLE 14

3α-Hydroxy-21-methyl-5α-pregnane-11,20-dione

3α-Hydroxy-21-methylene-5α-pregnane-11,20-dione(850 mg) was hydrogenated over 10% palladium on carbon catalyst (80 mg) in ethyl acetate for 1 hour. The catalyst was filtered off and the solvent removed in vacuo to give title compound (800 mg) as a white solid identical with the material of Example 1.

EXAMPLE 15

3α-Hydroxy-21-methoxymethyl-5α-pregnane-11,20-dione

3α-Hydroxy-21-morpholinomethyl-5α-pregnane-11,20-dione (600 mg) was dissolved in methanol (30 ml) and methyl iodide (2 ml) added to the solution. The mixture was refluxed for 3 hours. A further quantity of methyl iodide (2 ml) was added and reflux continued for 1 hour. The mixture was poured into water, extracted with ethyl acetate, and the extract washed with water, dried ($Na_2SO_4$) and evaporated to a white foam which was purified by preparative t.l.c. (ethyl acetate/petrol). to give a white foam. This was crystallised from ether to give title compound (140 mg) as off-white plates m.p. 97°–100° C $[\alpha]_D + 93.2°$ (c, 1.05).

EXAMPLE 16

21-Ethoxymethyl-3α-hydroxy-5α-pregnane-11,20-dione

3α-Hydroxy-21-methylene-5α-pregnane11,20 -dione (250 mg) was dissolved in ethanol (50 ml) and potassium bicarbonate solution (10%; 3 ml) added to the refluxing solution. After ¾ hour the mixture was poured into water, and extracted into ether. The extract was washed with water, dried ($Na_2SO_4$) and evaporated to a white solid (190 mg) which was recrystallised from ether to give title compound (120 mg) m.p. 126°–129.5° C $[\alpha]_D + 87.5°$ (c, 1.03).

EXAMPLE 17

21,21-Dimethyl-3α-hydroxy-5α-pregnane-11,20-dione

3α-Hydroxy-21-methylene-21-morpholinomethyl-5α-pregnane-11,20-dione (500 mg) was hydrogenated over 10% palladium on carbon (50 mg) in ethyl acetate. The catalyst was filtered off and the filtrate evaporated to a white foam. The foam was purified by preparative t.l.c. (ethyl acetate/petrol) to give title compound (180 mg) as a white foam $[\alpha]_D + 133°$ (c, 1.02).

EXAMPLE 18

21,21-Ethylene-3α-hydroxy-5α-pregnane-11,20-dione

Trimethylsulphoxonium iodide (640 mg) in dimethylsulphoxide (10 ml) was stirred with sodium hydroxide (70 mg) for 1 hour. 3α-Hydroxy-21-methylene-5α-pregnane-11,20-dione (500 mg) was added and the mixture stirred for 20 hours, poured into water and the precipitate filtered and purified by preparative t.l.c. (ethyl acetate/petrol) to give title compound (130 mg) as a white solid m.p. 158°–162° C $[\alpha]_D + 136°$ (c, 0.54).

EXAMPLE 19

21-Ethoxycarbonyl-3α-hydroxy-5α-pregnane-11,20-dione

3α-(Tetrahydropyran-2ξ-yloxy)-5α-pregnane-11,20-dione (0.9 g) in boiling diethyl carbonate (12 ml) under nitrogen was treated with 1 drop of ethanol and then sodium hydroxide (0.17 g). The mixture was refluxed for 20 minutes, then cooled and the excess sodium hydride was destroyed with ethanol. The reaction mixture was partitioned between water and ether. The organic layer was washed with water, dried ($MgSO_4$) and evaporated. The residue (1.0 g) was purified by preparative t.l.c. to give the ester (0.59 g) This ester in ethanol (5 ml) was treated with 2N hydrochloric acid (0.5 ml) and after ca 6 hours the reaction mixture was partitioned between water and ether. The organic layer was washed with water, dried ($MgSO_4$) and evaporated. The residue (0.6 g) was subjected to preparative t.l.c. (ethyl acetate/petrol 1:2). The more polar fraction (0.29 g) gave after crystallisation from ispropyl ether the title compound (0.08 g), m.p. 120-121°, $[\alpha]_D + 120.5°$, $\lambda_{max}$. 249 nm. ($\epsilon$ 4,250).

EXAMPLE 20

20-Ethoxy-21-formyl-3α-hydroxy-5α-pregn-20-en-11-one

A solution of 3α-acetoxy-20-ethoxy-21-formyl-5α-pregn-20-en-11-one (500 mg) in ethyl alcohol (15 ml) was treated with potassium bicarbonate (450 mg) and the mixture was refluxed, under nitrogen, for 7 hours, then poured into water. The product was extracted with methylene chloride, and the extract washed with water, dried and evaporated. Purification of the residue (37 mg) by preparative t.l.c. and crystallisation from methyl acetate/petrol gave title compound (154 mg) m.p. 175°–178°, $[\alpha]_D$ − 115.9°, $\lambda_{max.}$ 258 nm ($\epsilon$ 18,780).

EXAMPLE 21

3α-Hydroxy-21-methoxycarbonyl-5α-pregnane-11,20-dione

A solution of 21-ethoxycarbonyl-3α-hydroxy-5α-pregnane-11,20-dione 850 mg) in dry methyl alcohol (40 ml) was treated with potassium bicarbonate (1.02 g) and the mixture was refluxed, under nitrogen, for 1 hr., then poured into water. The product was extracted with ethyl acetate, and the extract washed with water, dried, and evaporated. The residue (506 mg) was purified by preparative t.l.c. and crystallisation from methyl acetate/petrol gave title compound (157 mg) m.p. 150°–152°, $[\alpha]_D$ + 111.2°, $\lambda_{max.}$ 248.5 nm ($\epsilon$ 4,185).

EXAMPLE 22

21-Formyl-3α-hydroxy-20-methoxy-5α-pregn-20-en-11-one

A solution of 3α-acetoxy-20-ethoxy-21-formyl-5α-pregn-20-en-11-one (500 mg) in dry methyl alcohol (15 ml) was treated with potassium bicarbonate (450 mg), and the mixture was refluxed, under nitrogen, for 4 hrs., then poured into water. The product was extracted with methylene chloride and the extract washed with water, dried and evaporated. The residue (472 mg) was subjected to preparative t.l.c. to give a 1:2 mixture of 20-ethoxy-21-formyl-3α-hydroxy-5α-pregn-20-en-11-one and 21-formyl-3α-hydroxy-20-methoxy-5α-pregn-20-en-11-one (257 mg).

This mixture was re-treated with methyl alcohol (8 ml) and potassium bicarbonate (259 mg), and refluxed under nitrogen for 6 hours. The reaction mixture was poured into water and the product was extracted with methylene chloride. The combined extracts were washed with water, dried and evaporated. The residue (191 mg) was purified by preparative t.l.c. (ethyl acetate/petrol) to give title compound (127 mg) $[\alpha]_D$ − 97.7°, $\lambda_{max.}$ 257 nm ($\epsilon$ 15,950).

EXAMPLE 23

3α-Hydroxy-21-dimethoxymethyl-5α-pregnane-11,20-dione

A solution of 21-formyl-3α-(tetrahydropyran-2ξ-yloxy)-5α-pregnane-11,20-dione (300 mg) in methyl alcohol (25 ml) was treated with perchloric acid (1.25 ml), and the mixture was stirred for 6 hours then poured into water. The product was extracted with ethyl acetate and the combined extracts were washed with water, dried and evaporated in vacuo. The residue (275 mg) was purified by preparative t.l.c. and crystallisation from methyl acetate/petrol to give title compound (85 mg) 123°–125° $[\alpha]_D$ + 115.0° (c, 0.31).

EXAMPLE 24

21-Formyl-3α-hydroxy-5α-pregnane-11,20-dione

A solution of 3α-hydroxy-21-dimethoxymethyl-5α-pregnane-11,20-dione (900 mg.) in glacial acetic acid (13 ml) and water (1.3 ml) was stirred at 75° C for 6 hours, then poured into a mixture of ice and water. The product was collected, washed with water and dried in vacuo to give title compound (395 mg), $[\alpha]_D$ + 100.5° (c, 0.4), $\lambda_{max.}$ 268 nm ($\epsilon$ 6,325).

EXAMPLE 25

3α-Hydroxy-21-hydroxymethyl-5α-pregnane-11,20-dione

21-Formyl-3α-(tetrahydropyran-2ξ-yloxy)-5α-pregnane-11,20-dione (1.0 g), was added to 75 ml of reagent [prepared by refluxing overnight a solution of chloroiridic acid (200 mg) in 94% aqueous isopropanol (400 ml) and trimethyl phosphite (32 ml)] neutralised with triethylamine the mixture was refluxed for ½ hr., then poured into water. The product was extracted with ethyl acetate and the combined extracts were washed with water, dried (MgSO$_4$)and evaporated in vacuo. Purification of the residue (1.2 g) by preparative t.l.c. gave 21-hydroxymethyl-3α-tetrahydropyran-2ξ-yloxy)-5α-pregnane-11,20-dione (492 mg).

A solution of the tetrahydropyranyl derivative in ethyl alcohol (10 ml) was treated with 2N hydrochloric acid (1.0 ml) and the mixture was stirred for 4½ hours. then poured into water. The product was extracted with ethyl acetate and the combined extracts were washed with water, dried (MgSO$_4$) and evaporated in vauco Purification of the residue (371 mg) by preparative t.l.c. and crystallisation from methyl acetate gave title compound (159 mg) m.p. 156°–158°, $[\alpha]_D$ + 105.0° (c, 0.49).

EXAMPLE 26

21-Acetylthiomethyl-3α-hydroxy-5α-pregnane-11,20-dione.

3α-Hydroxy-21-methylene-5α-pregnane-11,20-dione (300 mg) was dissolved in thioacetic acid (2 ml) and left at room temperature for 3 hours. The mixture was poured into water and the precipitated oil extracted into ethyl acetate. The organic layer was washed with saturated sodium bicarbonate and water, dried over anhydrous sodium sulphate, evaporated to a pale yellow foam and purified by preparative t.l.c. in ethyl acetate/petrol (1:1). The main band gave title compound (150 mg) as an off-white foam. $[\alpha]_D$ + 60.5° (c 0.98).

EXAMPLE 27

3α-Hydroxy-21-morpholinoacetylthiomethyl-5α-pregnane-11,20-dione.

3α-Hydroxy-21-methylene-5α-pregnane-11,20-dione (500 mg) was dissolved in acetone (20 ml) and the solution treated with morpholinothioacetic acid (300mg), at reflux for 3 hours. The mixture was poured into water and the emulsion extracted with either. The extracts were washed with water, dried over anhydrous sodium sulphate and evaporated to a foam (540 mg) which was purified by preparative t.l.c. in ethyl acetate/petrol (1:1). The main band gave title compound (490mg.) as a white foam. $[\alpha]_D$ + 48° ($c$ = 1.03).

EXAMPLE 28

3α-Hydroxy-21-piperidinoacetylthiomethyl-5α-pregnane-11,20-dione.

A solution of 3α-hydroxy-21-methylene-5α-pregnane-11,20-dione (350 mg) in acetone (15 ml) was refluxed with piperidinothioacetic acid for ½ hour, poured into water and the suspension extracted into ethyl acetate. The extract was washed with water, dried over anhydrous sodium sulphate and evaporated to give title compound (400 mg) as a white foam. $[\alpha]_D +$ 50° ($c = 0.19$).

EXAMPLE 29

3α-Hydroxy-21-(2'-morpholino-n-valerylthiomethyl)-5α-pregnane-11,20-dione

Treatment of 3α-hydroxy-21-methylene-5α-pregnane-11,20-dione (240 mg) in acetone (10 ml) with 2-morpholinothiovaleric acid (150 mg) in similar manner to that described in Example 27 gave title compound (130 mg) as an off white foam $\lambda_{max}^{EtOH}$ 235,300nm. (ε3,600;273).

EXAMPLE 30

3α-Hydroxy-21-nicotinylthiomethyl-5α-pregnane-11,20-dione

Treatment of 3α-hydroxy-21-methylene-5α-pregnane-11,20-dione (240 mg) in acetone (15 ml) with thionicotinic acid (150 mg) for 4 hrs. in similar manner to that described in Example 27 gave title compound (220 mg) as a white foam $[\alpha_D] + 55.6°$ ($c$ 1.01).

EXAMPLE 31

21-Ethylthiomethyl-3α-hydroxy-5α-pregnane-11,20-dione

3α-Hydroxy-21-methylene-5α-pregnane-11,20-dione (250 mg.) was dissolved in ethanethiol (2 ml) and the solution kept at room temperature for 24 hours. The excess ethanethiol was removed in vacuo and the residue partitioned between ether and water. The ethereal solution was washed with water, dried over anhydrous sodium sulphate and evaporated to a foam which was purified by preparative t.l.c. to give title compound (150 mg) as a glass $[\alpha]_D + 83.3°$ ($c = 0.12$)

EXAMPLE 32

3α-Hydroxy-21-(2'-morpholinoethylthiomethyl)-5α-pregnane-11,20-dione

3α-Hydroxy-21-methylene-5α-pregnane-11,20-dione (250 mg) in morpholine ethanethiol (3 ml) was stirred at room temperature for 1 hour, poured into water and the oil formed extracted into ethyl acetate. The extracts were washed with water, dried over anhydrous sodium sulphate and evaporated to foam which was purified by preparative t.l.c. in acetone/petrol (1:1) run twice. The main band gave title compound (160 mg) as a foam which collapsed to a gum $[\alpha]_D + 68.7°$ ($c = 0.16$).

EXAMPLE 33

3α-Hydroxy-21-(pyrid-2'-ylthiomethyl)-5α-pregnane-11,20-dione

3α-Hydroxy-21-methylene-5α-pregnane-11,20-dione (250 mg) was dissolved in acetone (20 ml) and the solution refluxed with 2-mercaptopyridine (160 mg) for 1 hour. The mixture was poured into water and the emulsion extracted into ethyl acetate. The extract was washed with water, dried over anhydrous sodium sulphate and evaporated to a foam which was purified by preparative t.l.c. in ethyl acetate/petrol (1:1). The main band ($R_f$ 0.3) gave title compound (210 mg) as an off white foam $[\alpha]_D + 58.4°$ ($c = 1.08$).

EXAMPLE 34

3α-Hydroxy-21-pyrimidin-2'-ylthiomethyl-5α-pregnane-11,20-dione

3α-Hydroxy-21-methylene-5α-pregnane-11,20-dione (300 mg) in acetone (40 ml) was treated at reflux with 2-mercaptopyrimidine (200 mg) for 30 min. The mixture was poured into water and the emulsion extracted with ether. The extracts were washed with water, dried over anhydrous sodium sulphate and evaporated to a yellow solid which was purified by preparative t.l.c. in ethyl acetate/petrol (1:1). The main band gave after crystallisation from acetone/petrol title compound (230 mg) as fine white needles, m.p. 175°–177° $[\alpha]_D + 64.6°$ ($c$ 32 1.14).

EXAMPLE 35

3α-Hydroxy-21-morpholinoacetoxymethyl-5α-pregnane-11,20-dione

3α-Hydroxy-21-iodoacetoxymethyl-5α-pregnane-11,20-dione (230 mg) in dry dichloromethane (25 ml) was treated with morpholine (1.0 ml) and the solution was stirred at room temperature for 30 minutes. The solution was diluted with dichloromethane, washed twice with water, dried over sodium sulphate and evaporated to a colourless gum (230 mg) which was purified by preparative t.l.c. in acetone/petrol 1:1. The main band was separated to give title compound (172 mg) as a white foam, $[\alpha]_D + 79°$ ($c$ 0.68).

EXAMPLE 36

21-Diethylaminoacetoxymethyl-3α-hydroxy-5α-pregnane-11,20-dione

3α-hydroxy-21-iodo-acetoxymethyl-5α-pregnane-11,20-dione (235 mg) in dry dichloromethane (25 ml) was treated with diethylamine (1 ml) in similar manner to that described in Example 35 to give title compound (89 mg)$[\alpha_D] + 73°$ ($c$ 0.42).

EXAMPLE 37

3α-Hydroxy-21-(2'-morpholinoethoxymethyl)-5α-pregnane-11,20-dione

3α-Hydroxy-21-methylene-5α-pregnane-11,20-dione (500 mg) was dissolved in N,β-hydroxyethylmorpholine (5 ml) and 50% aqueous potassium hydroxide (0.2 ml) added to the solution. After 15 min. at room temperature, the mixture was poured into water and the emulsion extracted into ethyl acetate. The extracts were washed with water, dried over anhydrous sodium sulphate and evaporated to an oil (490 mg) which was purified by preparative t.l.c. in acetone. The main band ($R_f$ 0.3–0.4) gave title compound (270 mg.) as an oil. $[\alpha]_D + 71°$ ($c=0.315$).

EXAMPLE 38

21-Acetoxymethyl-3α-hydroxy-5α-pregnane-11,20-dione

21Hydroxymethyl-3α-tetrahydropyranyloxy-5α-pregnane-11,20- dione (600 mg) in anhydrous pyridine (12 ml) was treated with acetic anhydride (1.0 ml), and the solution was stirred at room temperature for 2½ hours. The solution was partitioned between hydrochloric acid (2N, 100 ml) and ether/ethyl acetate 1/1, and the organic phase was washed with water, dried over sodium sulphate and evaporated to an oil (640 mg). The crude product (630 mg) was dissolved in I.M.S. (25 ml) and dilute hydrochloric acid (2N; 2.5 ml) was added. The solution was stirred at room temperature for 2 hours. The solution was neutralised with 10% potassium bicarbonate solution (5 ml) and concentrated by evaporation until an oily solid began to separate. The mixture was then diluted with water and extracted twice with ether/ethyl acetate 1/1. The combined organic extract was washed with water, dried over sodium sulphate and evaporated to a pale yellow oil (500 mg) which as purified by preparative t.l.c. in ethyl acetate/petrol 1/1. The main band, $R_f$ 0.3 was separated to give 242 mg of solid which was recrystalized from ethyl acetate/petrol to give title compound (187 mg) as colourless plates, m.p. 113°–115°, $[\alpha]_D$ + 103° (c 1.32).

EXAMPLE 39

21-Chloroacetoxymethyl-3α-hydroxy-5α-pregnane-11,20-dione

To a solution of 21-hydroxymethyl-3α-tetrahydropyranyloxy5α-pregnane-11,20 -dione (1.43g) in pyridine (21 ml) was added chloroacetic anhydride (1.4g), and the solution was stirred at room temperature for 30 minutes. The solution was diluted with hydrochloric acid (2N; 150 ml) and the precipitate extracted into ether/ethyl acetate 1:1. The combined extract was washed with water, dried over sodium sulphate and evaporated to a yellow oil (1.8g).

This crude tetrahydropyranyl ether (1.8 gm) in IMS (50 ml) was treated with hydrochloric acid (2N 5 ml) in similar manner to that described in Example 38 to give after preparative t.l.c. an oil which was triturated with ether to give the title compound (542 mg) as off white crystals, m.p. 95-97°, $[\alpha_D]$ + 93° (c 0.92)

EXAMPLE 40

3α-Hydroxy-21-thiazolidinomethyl-5α-pregnane-11,20-dione

3α-Hydroxy-21-methylene-5α-pregnane-11,20-dione (250 mg) was dissolved in thiazolidine (2 ml) and the solution left at room temperature for 2 hours, then poured into water and the precipitated oil extracted into ethyl acetate. The extracts were washed with water, dried over anhydrous sodium sulphate and evaporated to a foam (280 mg) which was purified by preparative t.l.c. in ethyl acetate. The main band gave title compound (110 mg ) as a white foam $[\alpha]_D$ + 84.5° (c =0.69).

EXAMPLE 41

21-Diethoxymethyl-3α-hydroxy-5α-pregnane-11,20-dione

A solution of 21-formyl-3α-(tetrahydropyran-2ξ-yloxy) -5α-pregnane-11,20-dione (1.0g.,) in ethyl alcohol (20 ml) was treated with 2N hydrocholoric acid, and the mixture was stirred for 7 hrs. then poured into water. The product was extracted with ethylacetate and the combined extracts were washed with water, dried (MgSO4) and evaporated in vacuo. The residue (1.02 g) was subjected to preparative t.l.c. to give title compound (190 mg) $[\alpha]_D$ + 94.9° (c 0.43).

EXAMPLE 42

21-Chloromethyl-3α-hydroxy-5α-pregnane-11,20-dione

3α-Hydroxy-21-methylene-5α-pregnane-11,20-dione (500 mg) was dissolved in dioxan (40 ml) and dry hydrogen chloride passed through the solution for 1 hour. The mixture was left to stand for a further 2 hours, then poured into water and the sticky solid extracted into ether. The extracts were washed with saturated sodium bicarbonate, water and then dried over anhydrous sodium sulphate. After evaporation and trituration of the resulting foam with ether/petrol the title compound (375 mg) was obtained as a white solid. m.p. 110°–112° with gas evolution $[\alpha]_D$ + 100° (c = 1.06).

EXAMPLE 43

21-Ethyl-3α-hydroxy-5α-pregnane-11,20-dione

Methyl lithium in ether (~1.3M: 7.5 ml) was added slowly to a slurry of cuprous iodide (950 mg) in dry ether (40 ml) under nitrogen at −20°, the initial yellow precipitate just redissolving. 3α-Hydroxy-21-methylene-5α-pregnane-11,20-dione (500 mg) in dry ether (10 ml) was added rapidly to the solution forming a yellow precipitate. After ¾ hr. at ~0° the mixture was poured into saturated ammonium chloride solution and the oily precipitate extracted with ether. The extracts were washed with saturated ammonium chloride solution, then water, and dried over anhydrous sodium sulphate. The dried solution was evaporated to an off white foam (430 mg) which was purified by preparative t.l.c. in ethyl acetate/petrol (1:1). The main band ($R_f$ ~ 0.4) gave a white foam which on trituration with petrol, containing a small quantity of ether, gave title compound (320 mg.) as a white solid, m.p. 112°–113°, $[\alpha]_D$ + 105° (c = 1.01).

EXAMPLE 44

3α-Hydroxy-21-phthalimidomethyl-5α-pregnane-11,20-dione

21-Chloromethyl-3α-hydroxy-5α-pregnane-11,20-dione (600 mg) in acetone was treated at reflux with potassium phthalimide (600 mg) for 10 hours, poured into water and the oily precipitate extracted into ether. The extracts were washed with water, dried over anhydrous sodium sulphate and evaporated to a white foam (700 mg). Purification by preparative t.l.c. in ethyl acetate/petrol (1:1) gave a foam which on trituration with ether gave title compound (490 mg) as a white solid m.p. 187°–189° $[\alpha]_D$ + 58.8° (c = 0.97).

EXAMPLE 45

3α-Hydroxy-21-morpholinomethyl-5α-pregnane-11,20-dione-citrate salt

3α-Hydroxy-21-morpholinomethyl-5α-pregnane-11,20-dione (108 mg., 2.5 mmole) was dissolved in ethanol (2 ml) and the solution was treated with 0.1M aqueous citric acid (2.5 ml; 2.5 mmole). The solution was evaporated below 40° and the residue dried in vacuo to constant weight. Water (2 ml) was added and the solution was filtered. The trace of filtered solid was washed with water (2 ml.) then dissolved in chloroform and the solution evaporated and dried in vacuo to give a residue of 1 mg. It was therefore assumed that the aqueous filtrates contained 107 mg. of steroidal base, so these were combined and diluted to 10.7 ml. to give a solution, concentration 10 mg/ml. w.r.t. steroid free base, pH 3.6.

EXAMPLE 46

0.05 gm of 3α-hydroxy-21-methoxymethyl-5α-pregnane-11,20-dione were dissolved in 2 ml of acetone at 20° C. The resulting solution was added to 2 gm of Cremphor EL at 20° C and stirred until homogeneous. The acetone was removed by a vigorous stream of nitrogen. The solution was diluted with sterile distilled water containing 0.05 gm of sodium chloride to give a final volume of 10 ml.

PREPARATION 1

21-Methyl-5α-pregnane-3,11,20-trione

A solution of 20β,21-epoxy-3α-hydroxy-5α-pregnan-11-one 3-nitrate (2.0 g.) in dry ether (300 ml) was added to a solution of lithium dimethyl cuprate in ether prepared by adding a solution of methyl lithium (31 ml of a 2 M solution) in ether to a stirred slurry of cuprous iodide (6.0 g.) in dry ether (100 ml.) under nitrogen at −20°. The resulting mixture was stoppered and left at 0° for 2 days and then poured into saturated aqueous ammonium chloride. The product was extracted into ethyl acetate and the extracts were washed with water, dried ($Na_2SO_4$) and evaporated. A solution of the residue (1.6 g.) in acetone (110 ml) was treated with a solution of potassium dichromate (3.4 g) in 2N-sulphuric acid (30 ml.) at room temperature for 30 min. The mixture was then poured into water (1 l.) and the precipitated solid was collected by filtration, washed with water and dried in vacuo. The crude material was purified by preparative t.l.c. (EtOAc/petrol) and crystallisation from acetone to give title compound as white prisms (664 mg), m.p. 148°; $[\alpha]_D + 127°$ (c 1.1).

PREPARATION 2

3α-Nitro-oxy-11-oxo-5α-androstane-17β-carboxylic acid

Fuming nitric acid (13 ml.) was added slowly with stirring to acetic anhydride (40 ml.) between −5° and 0°. This nitrating mixture was stirred with a solution of 3α-hydroxy-11-oxo-5α-androstane-17β-carboxylic acid (8 g.) in chloroform (240 ml.) for 1 hour, between −5° and 0°. The mixture was poured into 2N-sodium hydroxide solution and stirred for 30 minutes. The mixture was extracted with chloroform and the combined extracts were washed with water and evaporated to a residue. The residue was stirred for one hour with ethanol (50 ml.), ether (250 ml.) and water (500 ml.), the pH being adjusted to 10–11 with sodium hydroxide. The aqueous layer was acidified with hydrochloric acid and extracted with chloroform. The extract was washed with water, dried ($Na_2SO_4$) and evaporated to a residue. Crystallisation from chloroform and benzene gave title compound (4.707 g.) as colourless rods, m.p. 214°–218° (dec.), $[\alpha]_D + 73°$.

PREPARATION 3

3α-Hydroxy-11-oxo-5α-androstane-17β-carboxylic acid

A solution of sodium hydroxide (2.1 g.) in water (18 ml.) was stirred at −5° and bromine (0.75 ml.) was added slowly, the temperature being maintained between −5° and 0°. Cold dioxan (12 ml.) was added. This sodium hypobromite solution was stirred at 0° until required.

3α-Hydroxy-5α-pregnane-11,20-dione (1.4 g.) was dissolved in dioxan (55 ml.) and water (16 ml.) and stirred at 5°. The sodium hypobromite solution was added and the mixture stirred for 3 hours between 5° and 10°.

Sodium sulphite heptahydrate (800 mg.) in water (5 ml.) was added and the mixture refluxed for 15 minutes.

The mixture was acidified hot with concentrated hydrochloric acid, filtered, evaporated until crystals appeared and extracted into chloroform. The extract was washed with water, dried and evaporated to a residue which was crystallised from benzene, chloroform and petrol to give title compound (660 mg.) as colourless needles; m.p. 265°–270°.

PREPARATION 4

21-bromo-3α-nitro-oxy-5α-pregnane-11,20-dione

A solution of 21-bromo-3α-hydroxy-5α-pregnane-11,20-dione (311 mg.) in chloroform (3 ml.) was added slowly with stirring to fuming nitric acid (0.8 ml.) and acetic anhydride (3 ml.), the temperature being kept between −5° and −10° for 1 hour. The solution was then poured into stirred aqueous sodium hydroxide (15 ml. 2N NaOH in 50 ml. water) to yield a resultant solution of pH 4, which was extracted with chloroform washed with saturated sodium bicarbonate solution, water, dried ($Na_2SO_4$) and evaporated to a white solid (324 mg.). Recrystallisation of this solid from acetone and petrol yielded title compound (243 mg.) as lemon irregular prisms; m.p. 121°–128°; $[\alpha]_D + 108°$ (c 0.94).

PREPARATION 5

20β,21-epoxy-3α-nitro-oxy-5α-pregnan-11-one

A solution of 21-bromo-3α-nitro-oxy-5α-pregnane-11,20-dione (1.01 g.) in methanol (20 ml.) and dry tetrahydrofuran (20 ml.) was stirred with sodium borohydride (84 mg.) in water (4 ml.) at room temperature. After one hour, glacial acetic acid (0.1 ml.) was added and the resultant solution was stirred, under nitrogen, with 2N sodium hydroxide (4 ml.). After ½ hour, the solvent was evaporated and the residue was stirred with water (200 ml.) for thirty minutes, filtered, washed with water and dried (756 mg.). Recrystallisation of the crude product from ether yielded title compound (275 mg.) as white rods; m.p. 147°–159°; $[\alpha]_D + 23.5°$ (c 1.02).

PREPARATION 6

3α-Hydroxy-21-methylene-21-morpholinomethyl-5α-pregnane-11,20-dione

3α-Hydroxy-5α-pregnane-11,20-dione (2 g) was dissolved in glacial acetic acid (50 ml). Paraformaldehyde (1.2 g), morpholine (2 ml) and conc. hydrochloric acid (2 ml) were added and the stirred mixture heated between 105°–110° C for 4 hours. The excess acetic acid was removed in vacuo and the red oil obtained partitioned between 0.1 N hydrochloric acid and ethyl acetate. The aqueous layer was basified with saturated sodium bicarbonate solution and the emulsion formed extracted into ethyl acetate. The organic layer was washed with water, dried ($Na_2SO_4$) and evaporated to a yellow foam which was purified by preparative t.l.c.

(ethyl acetate) to give title compound (550 mg) as a foam [α]$_D$ + 100° (c, 0.11).

PREPARATION 7

3α-Acetoxy-20-ethoxy-21-formyl-5α-pregn-20-en-11-one

A stirred solution of 3α-acetoxy-5α-pregnane-11,20-dione (0.375 g.) in ethyl orthoformate (10 ml) at 0° was treated with 9 drops of 75% perchloric acid over 20 minutes. Ca 10 drops of pyridine were then added and the mixture was extracted with ice-cold ether. The organic layer was washed with N hydrochloric acid solution, then aqueous sodium hydrogen carbonate and finally water. It was dried (MgSO$_4$) and evaporated. The residue (0.5 g) was purified by preparative t.l.c. (ethyl acetate/petrol, 1:3) and then crystallisation from methyl acetate/petrol to give the title compound (0.2 g), m.p. 150°–154°, [α]$_D$ − 59.8°, λ$_{max}$ 258.9 nm (ε 15,900).

PREPARATION 8

3α-(Tetrahydropyran-2ξyloxy)-5α-pregnane-11,20-dione

A solution of 3α-hydroxy-5α-pregnane-11,20-dione (1.0 g.) in redistilled dihydropyran (9.2 ml.) with dry chloroform (4 ml.) was cooled to 0° and a drop of phosphorus oxychloride added. The mixture was kept at room temperature for 25 minutes then diluted with ether (30 ml.) and washed with saturated sodium bicarbonate solution. Evaporation gave the crude product as a gum. Trituration with petrol and benzene-petrol finally gave the tetrahydropyranyl ether (0.325 g.) as small needles, m.p. 119°–122°, [α]$_D$ + 63.5° (c 0.99).

PREPARATION 9

3α-Acetoxy-5α-pregnane-11,20-dione

A solution of 3α-hydroxy-5α-pregnane-11,20-dione (1 g) in pyridine (ca 5 ml) was treated with acetic anhydride (2.5 ml) and allowed to stand overnight. The reaction mixture was poured into water and the solid collected by filtration and dried to give the title compound m.p. 150°–151°.

PREPARATION 10

21-Formyl-3α-(tetrahydropyran-2ξ-yloxy)-5α-pregnane-11,20-dione

Ethyl formate (0.7 ml) was added to a mixture of 3α-(tetrahydropyran-2ξ-yloxy)-5α-pregnane-11,20-dione (840 mg) and sodium hydride (130 mg) in dry dimethyl sulphoxide (15 ml). The mixture was stirred, under nitrogen for 1¼ hrs., then treated with methyl alcohol to destroy excess sodium hydride, and poured into dilute hydrochloric acid. The precipitate was collected, washed and dried to give title compound (943 mg).

PREPARATION 11

3α-Hydroxy-21-iodoacetoxymethyl-5α-pregnane-11,20-dione

21-Chloroacetoxymethyl-3α-hydroxy-5α-pregnane-11,20-dione (400 mg.) in acetone (40 ml) was treated with sodium iodide (420 mg.) and the mixture was refluxed for 40 mins. The filtered solution was evaporated to a yellow solid which was partitioned between water and ether/ethyl acetate 1:1. The organic layer was washed with water, dried over sodium sulphate and evaporated to give title compound (500 mg) as a yellow foam.

We claim:
1. A 3α-hydroxy steroid of the pregnane or 19-norpregnane series selected from the group consisting of a compound of the formula:

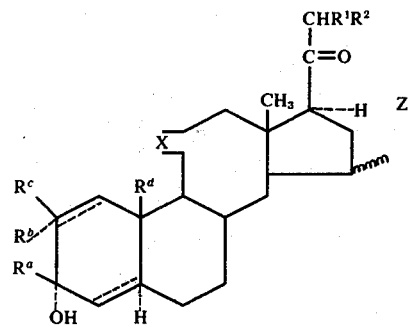

wherein R$^a$ is hydrogen or methyl; R$^b$ is hydrogen or when R$^c$ and R$^a$ are hydrogen, methyl; R$^c$ is hydrogen or, when R$^b$ and R$^a$ are hydrogen, a C$_{1-6}$ alkoxy or a C$_{1-5}$ alkyl group; R$^d$ is hydrogen or methyl; X is two hydrogen atoms or an oxo group; Z is hydrogen or methyl; and when the 2- and 3β-positions are unsubstituted the dotted lines at positions 1,2 and 4,5 represent an optional double bond at either one of these two positions; and R$^1$ is a hydrogen atom or a C$_{2-5}$ alkoxy carbonyl group; and when R$^1$ is a hydrogen atom, R$^2$ is a methyl group substituted by:

a. a group —NR$^6$R$^7$ where R$^6$ and R$^7$ taken together with the nitrogen atom represent a phthalimido group or an unsubstituted saturated 5–6 membered ring which may contain a sulphur or oxygen atom; or said 5-6 membered ring substituted by one or more methyl groups; or b. a hydroxyl group or C$_{1-6}$ alkoxy group which may be substituted by a group of the formula —NR$^6$R$^7$ where R$^6$ and R$^7$ taken together with the nitrogen atom represent an unsubstituted saturated 5–6 membered ring which may contain a sulphur or oxygen atom; or said 5-6 membered ring substituted by one or more methyl groups; or c. a group —O.CO.R$^5$ where R$^5$ is a C$_{1-5}$ alkyl group substituted by a group —NR$^6$R$^7$ as defined in (b) above or in which R$^6$ and R$^7$ may additionally be the same or different C$_{1-6}$ alkyl group;

d. a fluorine or chlorine atom; or e. a group —SR$^8$ where R$^8$ is a C$_{1-6}$ alkyl which may be substituted by a morpholino group or R$^8$ is a carbon-attached pyridyl or pyrimidyl group; or f. a group —SCOR$^9$ where R$^9$ is a C$_{1-6}$ alkyl group which may be substituted by a group —NR$^6$R$^7$ as defined in (b) above or R$^9$ is a carbon-attached pyridyl group; or R$^2$ is a C$_{1-5}$ alkanoyl group which may be substituted by a group —NR$^6$R$^7$ as defined in (b) above; or R$^2$ is a C$_{2-5}$ alkoxy carbonyl group or R$^2$ is a pyridine carbonyl group; or R$^2$ is a di(C$_{1-3}$) alkoxy methyl group; or R$^2$ is a group of the formula:

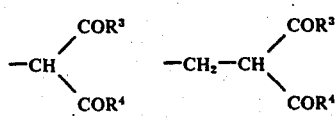

where $R^3$ and $R^4$ are the same or different and are $C_{1-4}$ alkyl or $C_{1-4}$ alkoxy groups; and when $R^1$ is $C_{2-5}$ alkoxy carbonyl, $R^2$ is a hydrogen atom or a $C_{2-5}$ alkoxy carbonyl group, or $R^1$ and $R^2$ may represent a $C_{1-6}$ alkylidene group or a $C_{2-6}$ divalent alkylene group; and the salts of those compounds having acidic or basic substituents.

2. A steroid as claimed in claim 1 which possesses a 5α-hydrogen atom.

3. A steroid as claimed in claim 1 which possesses an 11-oxo group.

4. A steroid as claimed in claim 1 said steroid being in the pregnane series.

5. A steroid as claimed in claim 1 wherein $R^1$ is a hydrogen atom and $R^2$ is a substituted methyl group.

6. A steroid as claimed in claim 1 wherein $R^1$ and $R^2$ taken together with the 21-carbon atom represent a cyclopropyl group.

7. A steroid as claimed in claim 1 which possesses a basic nitrogen atom, said steroid being in the form of a hydrochloride, hydrobromide, phosphate, sulphate, p-toluenesulphonate, methanesulphonate, citrate, tartrate, acetate, ascorbate, lactate, maleate or succinate.

8. A steroid as claimed in claim 1, said steroid being
21-ethoxycarbonyl-3α-hydroxy-5α-pregnane-11,20-dione;
3α-hydroxy-21-methoxycarbonyl-5α-pregnane-11,20-dione;
21-formyl-3α-hydroxy-20-methoxy-5α-pregn-20-en-11-one;
21-ethoxymethyl-3α-hydroxy-5α-pregnane-11,20-dione;
3α-hydroxy-21-methoxymethyl-5α-pregnane-11,20-dione; or
21,21-ethylene-3α-hydroxy-5α-pregnane-11,20-dione.

9. A steroid as claimed in claim 1, said steroid being
21-chloromethyl-3α-hydroxy-5α-pregnane-11,20-dione;
3α-hydroxy-21-thiazolidinomethyl-5α-pregnane-11,20-dione and its salts;
21-acetoxymethyl-3α-hydroxy-5α-pregnane-11,20-dione;
3α-hydroxy-21-morpholinoacetoxymethyl-5α-pregnane-11,20-dione and its salts;
3α-hydroxy-21-phthalimidomethyl-5α-pregnane-11,20,-dione;
3α-hydroxy-21-morpholinoacetylthio-5α-pregnane-11,20-dione;
3α-hydroxy-21-(pyrid-2-ylthiomethyl)-5α-pregnane-11,20-dione; or
3α-hydroxy-21-(pyrid-3-ylcarbonylthiomethyl)-5α-pregnane-11,20-dione.

10. A 3α-hydroxy steroid of the pregnane or 19-nor-pregnane series selected from the group consisting of a compound of the formula:

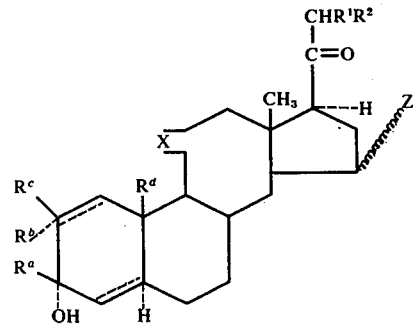

wherein:
$R^a$ is hydrogen or methyl; $R^b$ is hydrogen or when $R^c$ and $R^a$ are hydrogen, methyl; $R^c$ is hydrogen or, when $R^b$ and $R^a$ are hydrogen, a $C_{1-6}$ alkoxy or a $C_{1-5}$ alkyl group; $R^d$ is hydrogen or methyl; X is two hydrogen atoms or an oxo group; Z is hydrogen or methyl; and when the 2- and 3β-positions are unsubstituted the dotted lines at positions 1,2 and 4,5 represent an optional double bond at either one of these two positions; and $R^1$ is a hydrogen atom; $R^2$ is alkoxycarbonyl, alkoxymethyl, acyloxymethyl or acyl or an aminomethyl group in which the amino group is the N-attached residue of a heterocyclic amine.

11. A steroid as claimed in claim 1 wherein $R^1$ and $R^2$ form methylene.

* * * * *